US009558569B2

United States Patent
Zamyatin et al.

(10) Patent No.: US 9,558,569 B2
(45) Date of Patent: Jan. 31, 2017

(54) METHOD AND SYSTEM FOR SUBSTANTIALLY REDUCING CONE BEAM ARTIFACTS BASED UPON IMAGE DOMAIN DIFFERENTIATION IN CIRCULAR COMPUTER TOMOGRAPHY (CT)

(71) Applicant: TOSHIBA MEDICAL SYSTEMS CORPORATION, Otawara-Shi, Tochigi-Ken (JP)

(72) Inventors: Alexander Zamyatin, Hawthorn Woods, IL (US); Satoru Nakanishi, Utsunomiya (JP); Be-Shan Chiang, Austin, TX (US); Thomas Labno, Palatine, IL (US)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 44 days.

(21) Appl. No.: 14/457,267

(22) Filed: Aug. 12, 2014

(65) Prior Publication Data
US 2016/0048983 A1 Feb. 18, 2016

(51) Int. Cl.
*G06T 11/00* (2006.01)
*A61B 6/00* (2006.01)
*A61B 6/03* (2006.01)
*A61B 6/02* (2006.01)

(52) U.S. Cl.
CPC .............. *G06T 11/006* (2013.01); *A61B 6/027* (2013.01); *A61B 6/032* (2013.01); *A61B 6/4085* (2013.01); *A61B 6/5258* (2013.01); *G06T 11/008* (2013.01); *G06T 2211/404* (2013.01); *G06T 2211/421* (2013.01); *G06T 2211/424* (2013.01)

(58) Field of Classification Search
CPC .... G06T 11/003; G06T 11/005; G06T 11/006; G06T 11/008
See application file for complete search history.

(56) References Cited

U.S. PATENT DOCUMENTS

| 7,251,307 | B2 * | 7/2007 | Chen | G06T 11/006 |
| | | | | 378/21 |
| 7,613,275 | B2 * | 11/2009 | Li | A61B 6/032 |
| | | | | 378/4 |
| 8,787,646 | B2 * | 7/2014 | Schaefer | A61B 6/032 |
| | | | | 382/131 |
| 9,245,320 | B2 * | 1/2016 | Zeng | G06T 11/005 |
| 2006/0227928 | A1 * | 10/2006 | Timmer | G06T 11/005 |
| | | | | 378/4 |

(Continued)

*Primary Examiner* — Utpal Shah
(74) *Attorney, Agent, or Firm* — Kenichiro Yoshida

(57) ABSTRACT

Cone beam artifacts arise in circular CT reconstruction. The cone beam artifacts are substantially removed by reconstructing a reference image from measured data at circular source trajectory, differentiating the reference image; generating synthetic data by forward projection of the differentiated reference image along a pre-determined source trajectory, which supplements the circular source trajectory to a theoretically complete trajectory, reconstructing a correction image from the synthetic data and optionally applying a scaling factor. Ultimately, the cone beam artifact is substantially reduced by generating a corrected image using the reference image and the correction image that has been optimally scaled based upon the adaptively determined scaling factor value.

19 Claims, 9 Drawing Sheets

(56) References Cited

U.S. PATENT DOCUMENTS

| | | | |
|---|---|---|---|
| 2009/0028288 A1* | 1/2009 | Horiuchi | A61B 6/032 378/4 |
| 2010/0232673 A1* | 9/2010 | Keck | A61B 6/502 382/132 |
| 2010/0283779 A1* | 11/2010 | Chiang | G06T 11/006 345/419 |
| 2012/0308100 A1* | 12/2012 | Pack | G06T 11/006 382/131 |
| 2013/0101192 A1* | 4/2013 | Nakanishi | G06T 11/006 382/131 |

* cited by examiner

METHOD AND SYSTEM FOR SUBSTANTIALLY REDUCING CONE BEAM ARTIFACTS BASED UPON IMAGE DOMAIN DIFFERENTIATION IN CIRCULAR COMPUTER TOMOGRAPHY (CT)

A related patent application Ser. No. 13/276,841 has been filed on Oct. 19, 2011 for disclosing a method and system for reducing cone beam artifacts.

FIELD OF THE INVENTION

The current invention is generally related to an image processing and system, and more particularly related to substantially reducing artifacts in cone beam Computer Tomography (CT).

BACKGROUND OF THE INVENTION

Cone beam artifacts are a well known problem in computed tomography. The cone angle of the X-ray source in most advanced CT systems such as Toshiba AquilionONE is quite large, and CFK images tend to suffer cone beam artifacts due to missing data in radon domain.

In one prior art approach, the artifact in circular cone beam CT is substantially removed by applying exact reconstruction based upon a theoretically complete trajectory such as a combination of a circular trajectory and a line trajectory. Although an additional line scan achieves a theoretically complete trajectory with a circular trajectory for exact reconstruction, the additional scan is often either unavailable or impractical to collect. Furthermore, since circular data and line data are not simultaneously obtained, any change in motion or agent enhancement between the two scans causes data inconsistency between the two data sets and affect image accuracy. Lastly, the additional scan undesirably exposes a patient to an additional dose of radiation.

For the above reasons, it is of particular interest to accurately reconstruct image volume only from circular data. In one prior art approach, a scanogram is used to estimate line data. Although this approach does not increase patient's radiation dose, cone beam artifacts are still observable even after the estimated line data generally helps reduce much of the artifacts. At the same time, any change in motion or agent enhancement is also causing some inaccuracy in the resulted images based upon a scanogram.

The above specified related patent application has disclosed another way to estimate the line data based upon a large image that is extended along a predetermined axis so that an improved image is reconstructed from the circular data and the estimated line data. The large image also has a field of view (FOV) that is larger than a desired FOV and is extended in the Z direction to generate the extended large image. Although a scaling factor is optionally used, a value of the scaling factor has been determined prior to the reconstruction for reconstructing an improved image.

In the above described techniques, it is still desired to have additional improvement in a system and a method for substantially reducing artifacts in circular cone beam Computer Tomography (CT).

BRIEF DESCRIPTION OF THE DRAWINGS

FIG. 8A is an original FDK image Image [x,y,z] with a field of view of 500 mm with 512×512×320.

FIG. 8B is a z difference image (DDZ) that has been generated by differentiating a difference between two slices along the z direction.

wherein the image IMAGE was forward projected (FP) first to and then the line data is differentiated.

Figure 9B:
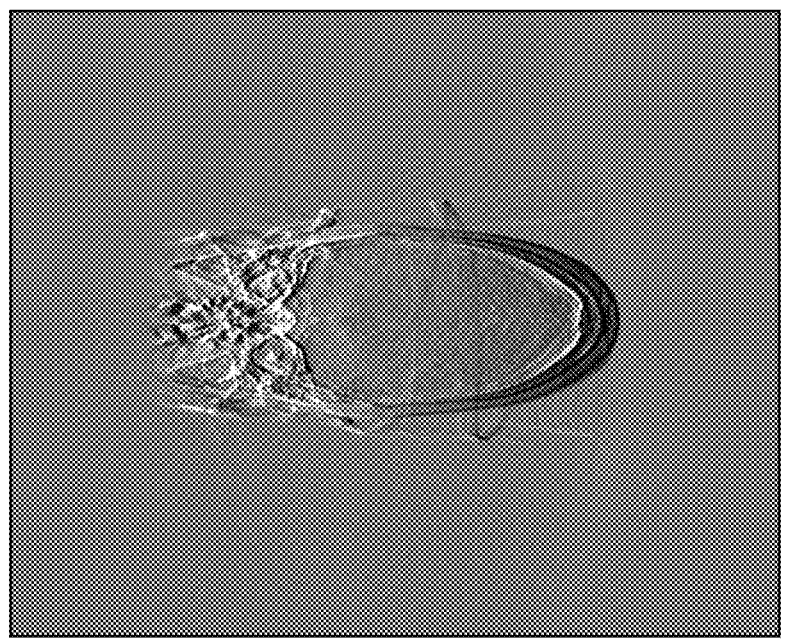
FIG. 9A is a first reconstructed image that is defined by $$\frac{d}{dh} FP[\text{IMAGE}],$$

FIG. 9B is a second reconstructed image that is defined by $$FP\left[\frac{d}{dz}\text{IMAGE}\right],$$

in which a z difference image (DDZ) is generated by differentiating a difference between two slices along the z direction and the derivative is forward projected (FP).

DETAILED DESCRIPTION OF THE EMBODIMENT(S)

Figure 1:
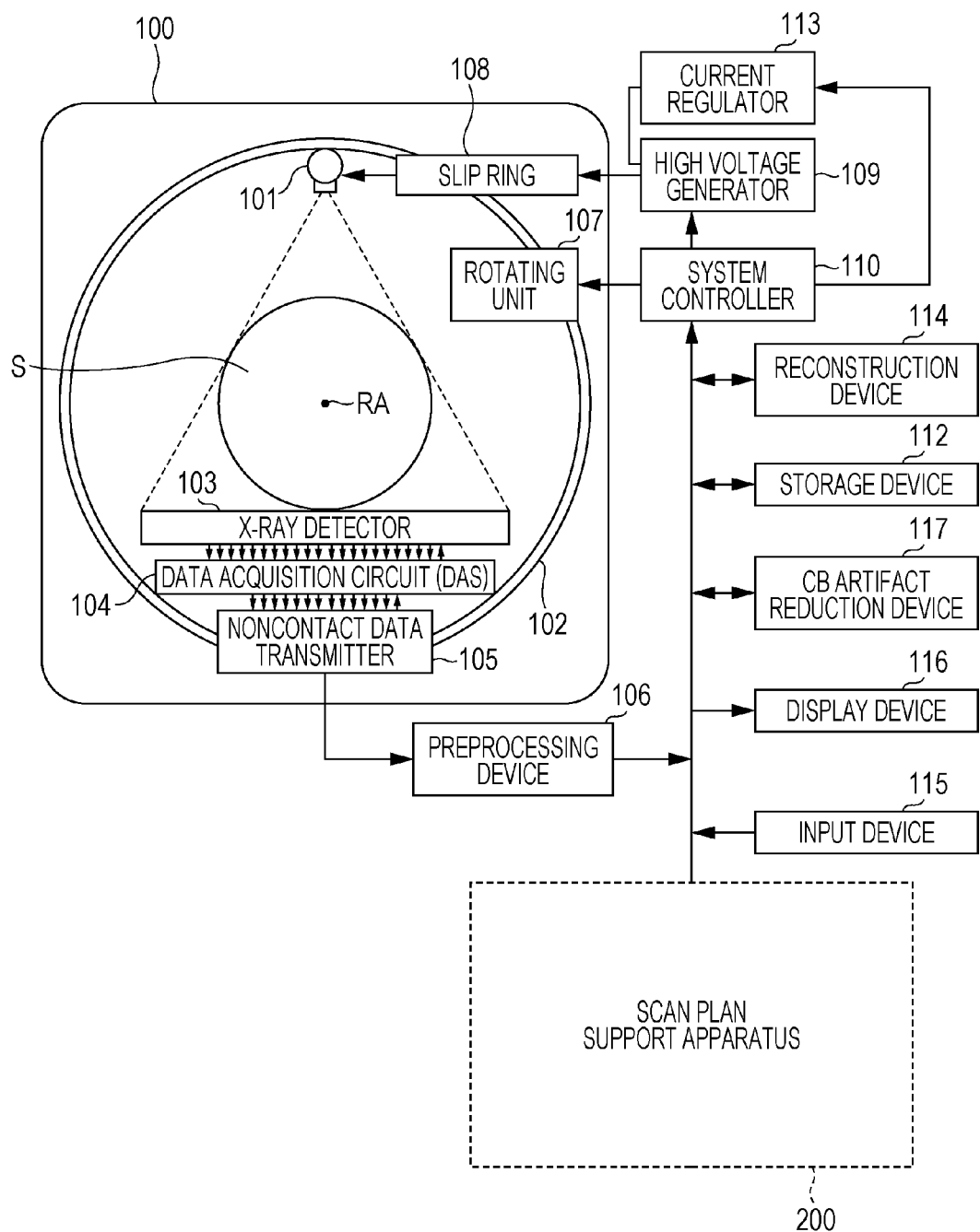
FIG. 1 is a diagram illustrating one embodiment of the multi-slice X-ray CT apparatus or scanner for substantially reducing cone-beam artifacts in images reconstructed from data acquired over circular trajectory according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116, multi-scale processing device 117 and the scan plan support apparatus 200. The scan plan support apparatus 200 includes a function for supporting an imaging technician to develop a scan plan.

One embodiment of the reconstruction device 114 further includes various software and hardware components and performs a predetermined analytic reconstruction process on the projection data. According to one aspect of the current invention, the reconstruction device 114 of the CT apparatus advantageously reconstructs an image volume by using a predetermined filtered backprojection (FBP) technique.

According to another aspect of the current invention, the reconstruction device 114 of the CT apparatus advantageously minimizes total variation (TV) using an iterative reconstruction technique. In general, the reconstruction device 114 in one embodiment of the current invention operates the total variation iterative reconstruction (TVIR) algorithm, which performs on the projection data simultaneous algebraic reconstruction such an ordered subset simultaneous algebraic reconstruction technique (OS-SART) step and regularization such as a TV minimization step. The two steps are sequentially implemented in the main loop where a number of iterations were prescribed in one embodiment.

Before the TV minimization step, the projection data undergoes an ordered subsets simultaneous algebraic reconstruction technique (OS-SART). The projection data is grouped into a predetermined number of subsets N each having a certain number of views. During the ordered subsets simultaneous algebraic reconstruction technique (OS-SART), each subset may be sequentially processed in one embodiment. In another embodiment, a plurality of the subsets may be processed in parallel by taking advantage of certain microprocessor such as multiple central processing units (CPU) or a graphics processing unit (GPU). In the total variation (TV) minimization step, one embodiment of the reconstruction device 114 employs a line search strategy to search a positive step size so as to ensure the objective function of the current image volume to be smaller than that of the previous image volume.

During the ordered subsets simultaneous algebraic reconstruction technique (OS-SART), the reconstruction device 114 also performs two major operations. Namely, for each subset N, the reconstruction device 114 reprojects the image volume to form the computed projection data and back-projects the normalized difference between the measured projection and the computed projection data to reconstruct an updated image volume. In further detail, one embodiment of the reconstruction device 114 reprojects the image volume by using the ray tracing technique where no coefficient of the system matrix is cached. Moreover, one embodiment of the reconstruction device 114 simultaneously reprojects all rays in a subset, and this is optionally implemented in parallel. In the back-projection, one embodiment of the reconstruction device 114 uses a pixel-driven technique to back-project all of the normalized difference projection data in a subset to form the desired updated image volume. Because the reconstruction device 114 back-projects all ray sums, i.e., difference projection data, in a subset to form an image volume, this operation is also optionally implemented in parallel. These operations are applied to every subset N to complete a single OS-SART step. In addition, AWAD is optionally combined.

In addition to the above described components, one embodiment of the current invention further includes various other software modules and hardware components for performing cone beam artifact reduction. According to one aspect of the current invention, a cone beam (CB) artifact reduction device 117 of the CT apparatus advantageously performs cone beam artifact reduction functions for substantially reducing cone beam artifacts under certain situations. In general, the CB artifact has two components including shading and high-contrast cone beams that degrade the image quality. To improve the image quality, shading is corrected by filtering rebinning while high-contrast is corrected by line image in one exemplary process.

In another embodiment of the current invention, the cone beam (CB) artifact reduction device 117 of the CT apparatus advantageously combines elements of exact reconstruction and iterative reconstruction such as SART to substantially reduce the cone beam artifact. As will be described in more detail, the reconstruction device 114 reconstructs a circular image from the measured projection data that has been acquired using a cone beam source over the circular source trajectory. Subsequently, the CB artifact reduction device 117 differentiates the circular image within the image domain and then forward projects line data from the differentiated circular image for improving efficiency and image quality. The reconstruction device 114 reconstructs a line image based upon the forward projected line data that had been differentiated before the forward projection. Based upon the above steps, the CB artifact reduction device 117 combines the circular image and the line image. The combined image contains substantially reduced CB artifacts, which otherwise exist in a conventionally reconstructed image. Finally, the CB artifact reduction device 117 outputs the corrected image.

In one embodiment according to the current invention, the cone beam artifact reduction device 117 is operationally connected to other software modules and or system components such as the storage device 112, the reconstruction device 114, the display device 116 and the input device 115 via a data/control bus. In this regard, the cone beam artifact reduction device 117 alone does not necessarily perform the cone beam artifact reducing functions and or their associated tasks in other embodiments according to the current invention. Furthermore, the cone beam artifact reduction device 117 is optionally a part of other devices such as the reconstruction device 114 in alternative embodiments according to the current invention. Both the cone beam artifact reduction device 117 and the reconstruction device 114 are implemented in a variety of ways and are not limited to particular combination of software and hardware components.

Figure 2:
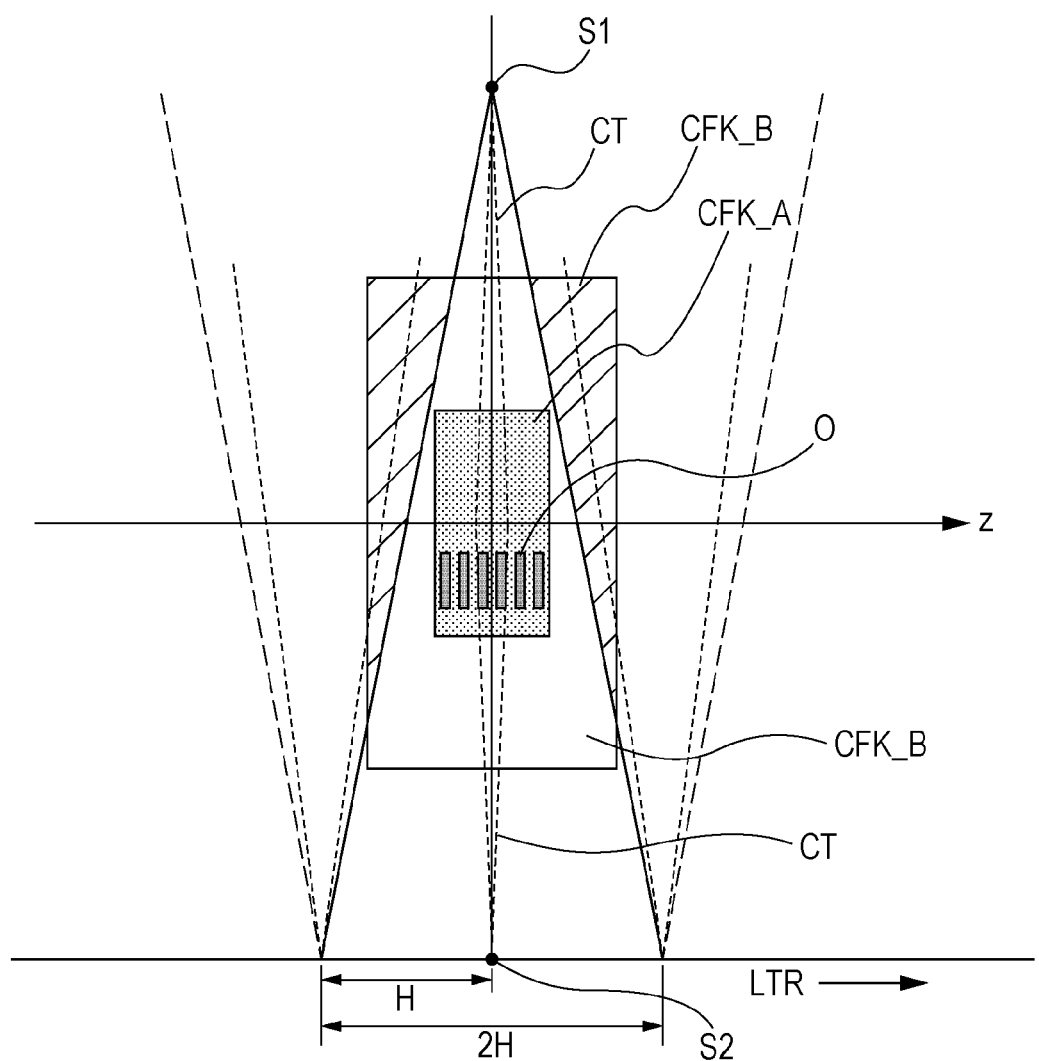
FIG. 2 is a diagram illustrating one aspect of the cause for cone beam (CB) artifacts to be substantially reduced by one embodiment according to the current invention.

FIG. 2 is a diagram illustrating one aspect of the cause for cone beam (CB) artifacts that are substantially reduced by one embodiment according to the current invention. The diagram illustrates an exemplary situation where a set of thin objects O is located at a relative position with respect to a source over a predetermined circular trajectory CT. Cone beam at a source position S1 emits toward the object O with a predetermined cone beam angle. The exemplary situation also illustrates that images are often reconstructed in a zoomed or desired field-of-view (FOV) with better resolution for a diagnostic purpose. Since information on an entire object attenuating the x-ray beam is necessary for forward projection, two volume images CFK_A and CFK_B are generated as illustrated in FIG. 2. The shaded areas correspond to insufficiently acquired measured data. The image CFK_A has the desired FOV to be used in a final result while the image CFK_B has a full FOV for generating missing line data. A required range 2H is shown along a line data direction LTR for generating the line data.

Figure 3:
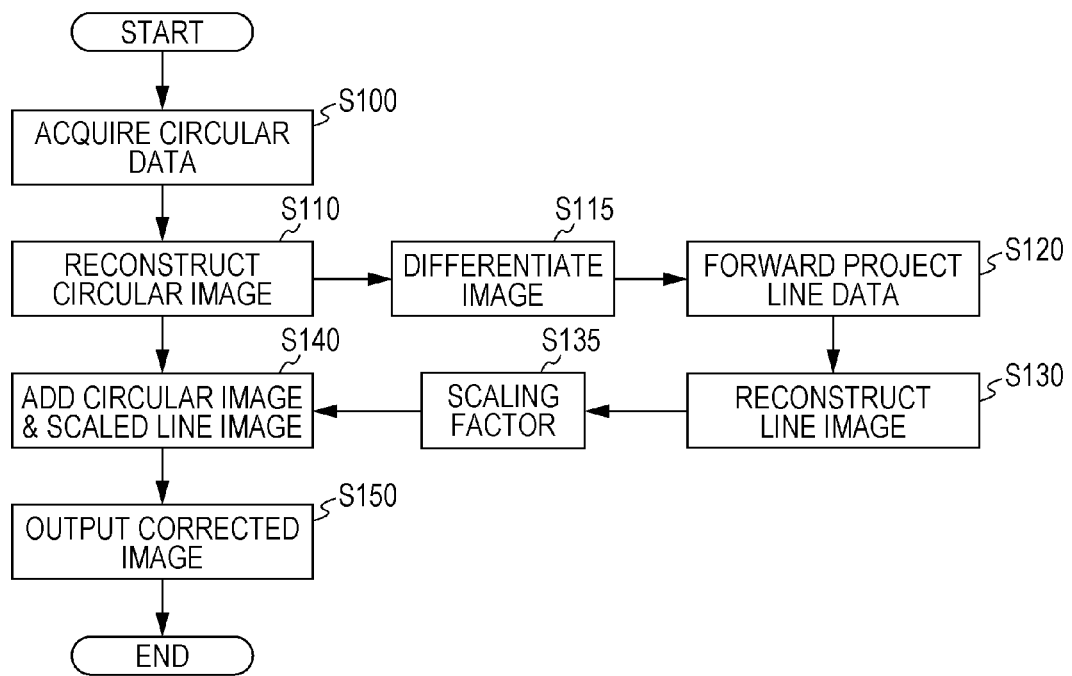
FIG. 3 is a flow chart illustrating general steps involved in an exemplary process of substantially reducing the cone beam (CB) artifacts by differentiating in the image domain according to the current invention.

Now referring to FIG. 3, a flow chart illustrates general steps involved in an exemplary process of substantially reducing the cone beam (CB) artifacts according to the current invention. In fact, the flow chart is a conceptual scheme of an exemplary process of substantially reducing the cone beam (CB) artifacts according to the current invention, and the current invention is not necessarily limited to the illustrated steps or acts as provided in the following description.

In a step S100, measured data is acquired with a cone beam source travelling over a predetermined circular trajectory. In general, the acquired measured data is susceptible to cone beam artifacts if an image is reconstructed in a conventional manner since the measured data is insufficient due to a cone beam circular scanning geometry. In a step S110, a circular image such as a Feldkamp, Davis, Kress (FDK) reconstruction image and a Hybrid convolution reconstruction (Hconv) image is reconstructed from the measured data that has been acquired using a cone beam source over a predetermined circular source trajectory. The reconstructed circular image is optionally stored in a predetermined storage to be retrieved later.

In a step S115, the circular image is differentiated in the image domain before forward projecting to obtain line data in step S120. Furthermore, no additional differentiation takes place after the step S115. In other words, differentiation is not performed after forward projection in the exemplary process of substantially reducing the cone beam (CB) artifacts according to the current invention. For example, a difference image is obtained along the predetermined Z axis from a CFK image with N slices. The difference is differentiated with respect to the z axis. In summary, the differentiation before forward projection in the exemplary process of substantially reducing the cone beam (CB) artifacts according to the current invention replaces differentiation after forward projection in the relevant prior art process.

In the steps S120 and S130, line data is generated from the differentiated image from the step S115 and a line image is reconstructed from the generated line data. In a step S120, line data is forward projected or reprojected from the circular image that has been reconstructed in the step S110 and then differentiated in the step S115. The detail of the line data generation in the step S120 will be later described with respect to another exemplary flow chart. In a step S130, a line image is reconstructed based upon the forward projected line data that has been generated in the step S120 but without any additional differentiation.

A scaling factor α is optionally used in a step S135. The scaling factor is applied to weigh the line image that has been reconstructed in the step S130. That is, a value of the scaling factor α is optionally either predetermined or calculated to ultimately reduce the cone beam artifact in a final image. In the step S135, the scaling factor a is optionally applied to the line image that has been reconstructed in the step S130 in order to generate a scaled line image.

Based upon the above steps S110, S115, S120, S130 and S135, the circular image and the processed line image are now combined in a step S140. The combined image contains substantially reduced CB artifacts, which otherwise exist in a conventionally reconstructed image. Finally, the corrected image is outputted in a step S150 for display or analysis. In another embodiment of the substantially reducing CB artifact, some of the above described steps are iteratively repeated using a known iterative technique such as SART to improve accuracy of the line data and in turn the artifact reduction in the outputted image.

Figure 4:
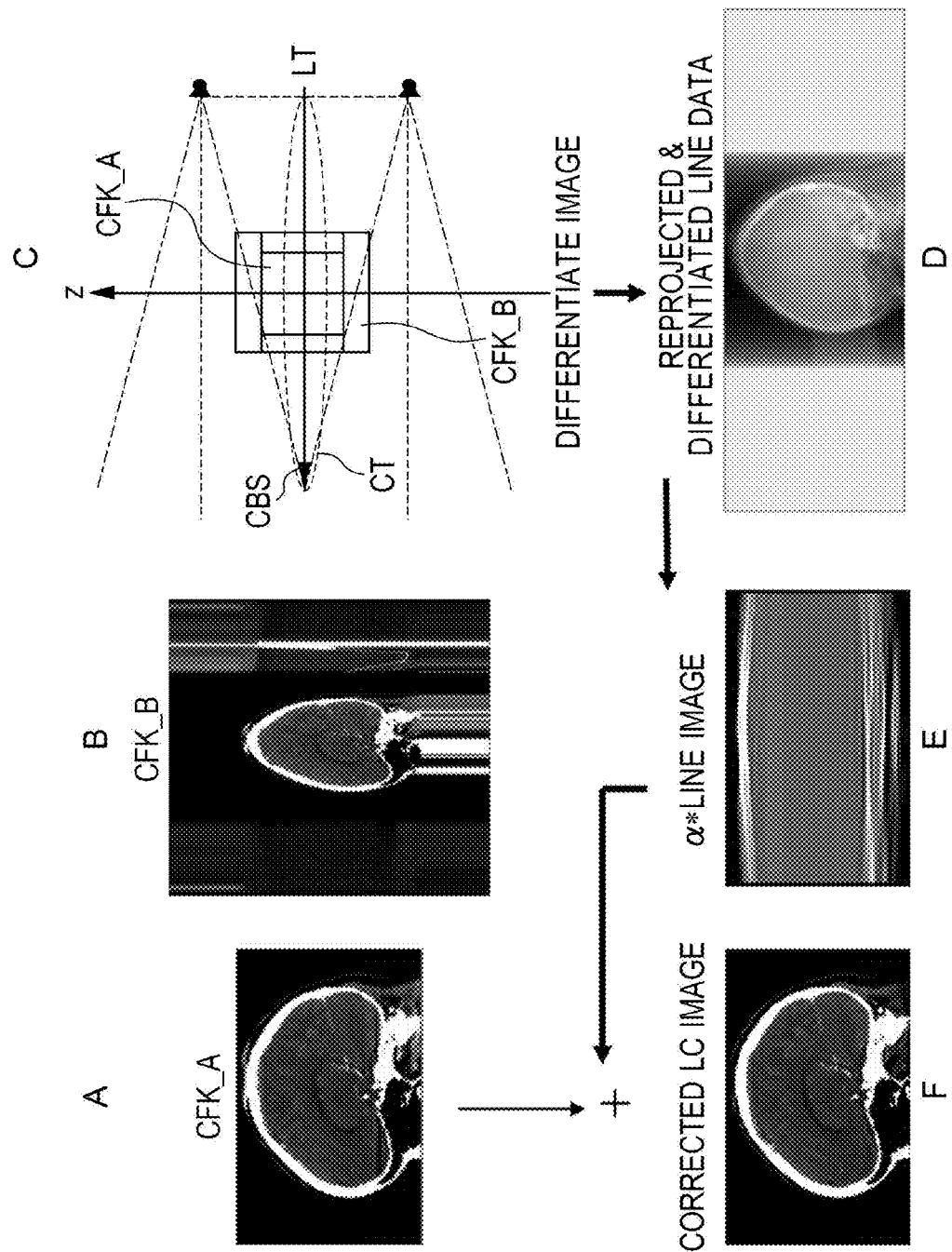
FIG. 4 is a collection of diagrams illustrating a certain conceptual solution for substantially reducing cone beam artifacts by differentiating in the image domain in one embodiment according to the current inventions.

FIG. 4 is a collection of diagrams illustrating a certain conceptual solution for substantially reducing cone beam artifacts by differentiating the image prior to forward projecting line data in one embodiment according to the current inventions. As already described with respect to FIG. 2, an exemplary situation requires a zoomed or desired field-of-view (FOV) with better resolution for a diagnostic purpose. Since information on an entire object attenuating the x-ray beam is necessary for forward projection, a first image CFK_A and a second image CFK_B as illustrated in FIGS. 4A and 4B are reconstructed using circular Feld-Kamp (CFK) technique from corresponding circular data that is acquired using a cone beam source CBS over the circular trajectory CT as illustrated in FIG. 4C. FIG. 4C also illustrates that the circular data for the image volume CFK_A is a zoomed portion of the circular data for the image CFK_B. That is, the image CFK_A has a desired FOV within a full or large FOV of the image CFK_B, and the full FOV is extended along the Z axial direction.

As indicated between FIGS. 4C and 4D, the image is differentiated before the image is reprojected. That is, the difference between two images is differentiated with respect to a predetermined axis. For example, a difference image is taken between two slices along the z axis at a predetermined pitch, and the difference image is differentiated with respect to the z axis. To get z difference image (Ddz) from a CFK image with N slices, there are generally two ways to implement. One implementation is to have Ddz image has N-1 slices, and the centers of the original CFK image and Ddz image are the same. In another implementation is to have Ddz image has N slices by padding a slice with zero values to all pixels, and the center of Ddz image is shifted by one half distance of one image slice in the z direction. Forward projected (i.e., reprojected) lines are not limited to a particular sampling pitch according to the current invention. In general, a forward projection line pitch is optionally set to a predetermined width or sparseness beyond a known prior art width range in one embodiment.

According to one embodiment, the line data as illustrated in FIG. 4D is generated by forward projection of the filtered back-projected volume image CFK_B that has been already differentiated prior to forward projection according to the current invention. In this regard, reprojection is synonymously used with forward projection in the above described line data generation in the current application. As described above, the second image CFK_B has a full FOV. Since x-rays with a large cone angle may pass through space in the Z direction beyond the reconstructed image, the image CFK_B is optionally extended over some Z-range that depends on the scanned system's cone angle. In other embodiments, to reduce the cone beam artifacts in the image CFK_B, a predetermined adaptive low-pass 3D filter is optionally applied to the image CFK_B before the forward projection along a line trajectory LT. Alternatively, a predetermined factorization approach is applied to the image CFK_B before the forward projection along a line trajectory LT in another embodiment.

After the line data is obtained by reprojection of the differentiated second image CFK_B from line trajectory, a line image with the desired FOV as illustrated in FIG. 4E is reconstructed from the line data as illustrated in FIG. 4D in one embodiment of the cone beam artifact reduction process or system according to the current invention. At the same time, the reconstructed line image is optionally weighed by a predetermined scaling factor α as also noted by the symbol in FIG. 4E. Finally, the line image with the desired FOV as illustrated in FIG. 4E is combined as indicated by a plus sign with the image volume CFK_A as illustrated in FIG. 4A to generate a corrected LC image as illustrated in FIG. 4F. The combined image LC has substantially reduced cone beam artifacts. In one embodiment, the image volume CFK_B is optionally updated by adding an image reconstructed from the line data with a full FOV. Furthermore, since the line data is forward projected from a volume image with artifacts, it is approximated data. For this reason, in another embodiment, an iterative approach is used to refine the line data and improve the cone beam artifact reduction.

Figure 5:
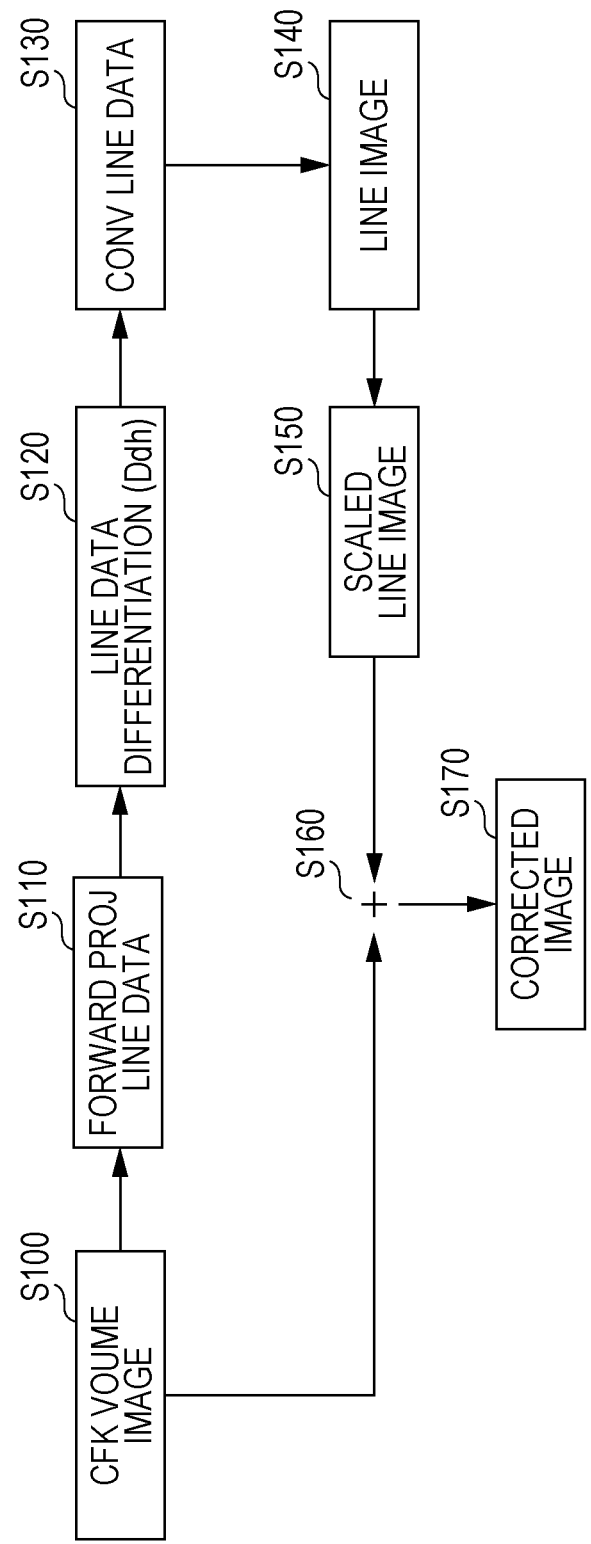
FIG. 5 is a flow chart illustrating steps involved in the cone beam artifact reduction process.
Figure 6:
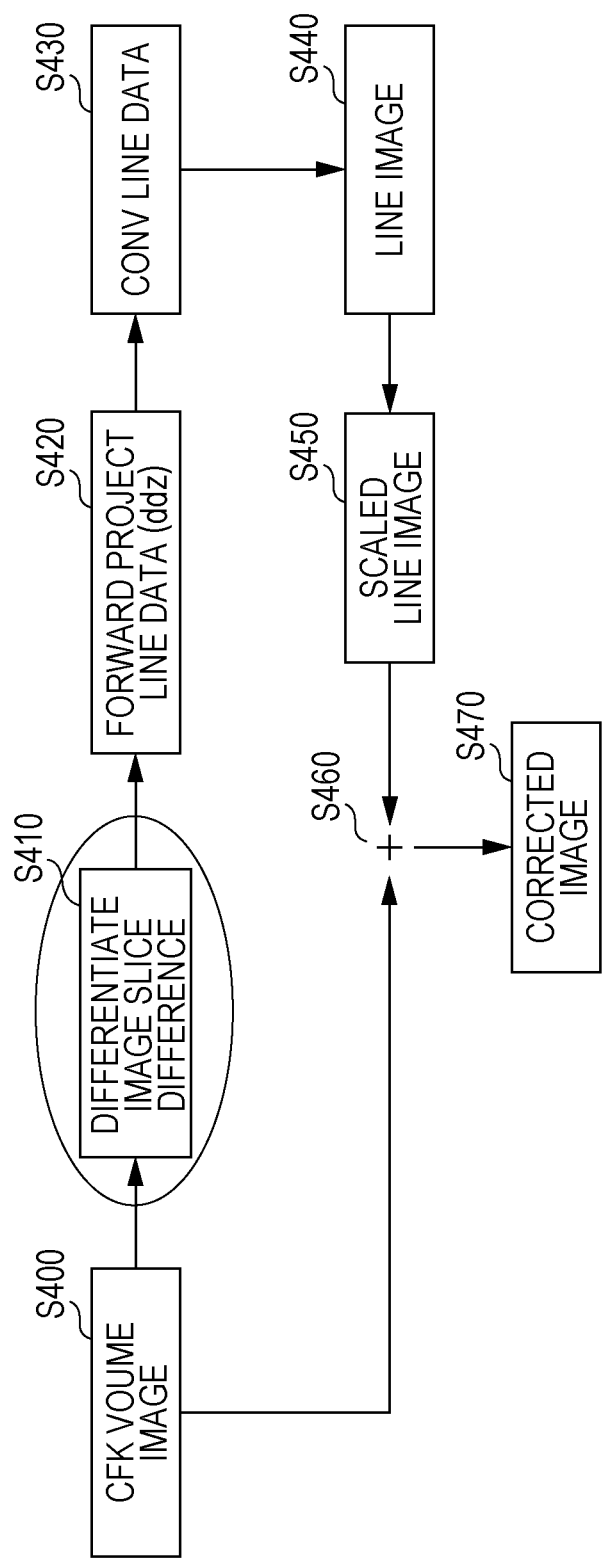
FIG. 6 is a flow chart illustrating steps involved in a cone beam artifact reduction process by differentiating in the image domain in one embodiment according to the current invention.

Referring to both FIGS. 5 and 6, two flow charts are provided to contrast two processes in order to elucidate the exemplary process of substantially reducing cone beam artifacts by differentiating the image prior to forward projecting line data according to the current invention. FIG. 5 is a flow chart illustrating steps involved in the cone beam artifact reduction process. On the other hand, FIG. 6 illustrates an exemplary process of substantially reducing cone beam artifacts by differentiating the image before forward projecting line data, In both processes, it is assumed that the measured data has been acquired by a predetermined circular data acquisition technique using a source travelling along a predetermined circular trajectory and having a certain conebeam angle.

Now referring to FIG. 5 in particular, the cone beam artifact reduction process generates reference image CFK in step S100, forward projects line data in step S110 and then differentiates the line data in step S120 before convolving the line data in step S130. The cone beam artifact reduction process generates line image by back projection in step S140 and optionally scales the line image in step S150 before adding in step S160 the optionally scaled line image from the step S150 and the original CFK volume image from the step S100 to output a corrected image in step S170.

In contrast, FIG. 6, one exemplary process of reducing the cone beam artifact according to the current invention generates reference image CFK in step S400, differentiates the image slice difference in step S410 before forward projection in a step S420. That is, the derivative is generated in the image domain before it is forward projected to generate line data in the step S420 and the line data is then convolved in step S430. The exemplary process of reducing cone beam artifact according to the current invention generates line image by back projection in step S440 and optionally scales the line image in step S450 before adding in step S460 the optionally scaled line image from the step S450 and the original CFK volume image from the step S400 to output a corrected image in step S470.

Figure 7:
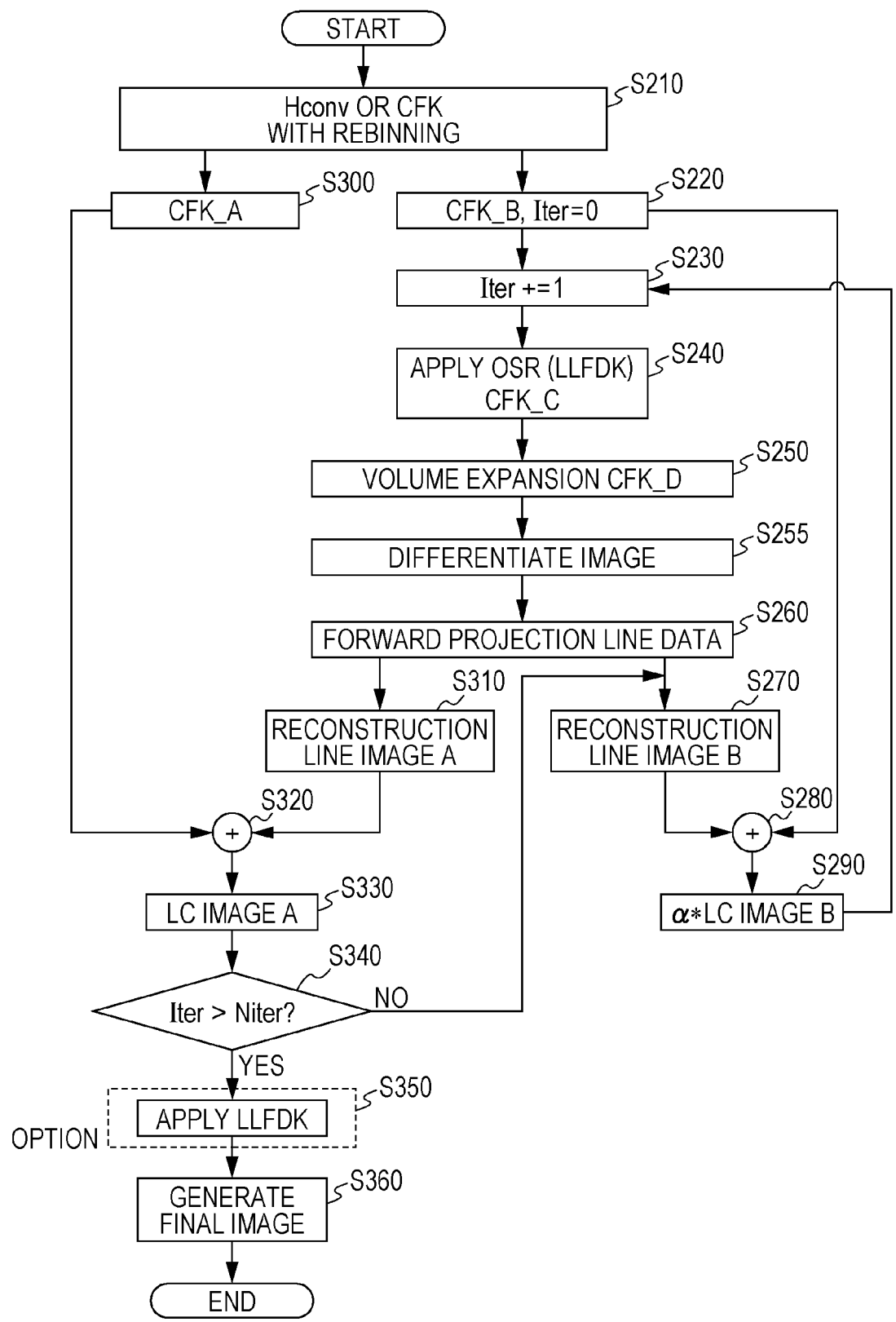
FIG. 7 is a flow chart illustrating detailed steps involved in one implementations of a cone beam artifact reduction process by differentiating in the image domain according to the current invention.

Now referring to FIG. 7, a flow chart illustrates exemplary steps of one specific implementation involved in a process of reducing cone beam artifact according to the current invention. The correction for the cone beam artifact is achieved by a combination of certain aspects of the implemented method and system according to the current invention. One aspect of correction is achieved because the predetermined source trajectory such as a line trajectory supplements the circular source trajectory of the reference image CFK_B. Furthermore, the cone beam artifact reduction process in the embodiment iteratively repeats certain steps such as steps S230 through S290 with respect to the line image so that a corrected image after a step S360 has substantially reduced cone beam artifacts according to the current invention. In alternative embodiments, the cone beam artifact reduction process performs line image manipulation in a predetermined manner in lieu of iteration.

Another aspect of correction is achieved by differentiating the image slice prior to forward projecting line data in one exemplary process according to the current invention. Since image slice differentiation is performed prior to forward projection in one exemplary process according to the current invention, it is more efficient than differentiating the line views which are generally more than a number of image slices. For example, one exemplary process according to the current invention differentiates 320 slices in stead of 800 line views after forward projection. The above described efficiency is further enhanced in certain data sets that have sparse views.

Another aspect of correction is that forward projected line data is generally improved in some characteristics such as quality and stability near the top and bottom slice boundaries in one exemplary process according to the current invention.

Still referring to FIG. 7, the exemplary process of substantially reducing the cone beam artifact is further described in detail by referring to its steps in one exelplary implementation according to the current invention. In general, reference images are obtained based upon a filtered-backprojection algorithm by filtering along predetermined filtering directions that are given by Cseg+z/cos (gamma), where gamma is a cone angle, z is a vertical distance from Cseg, which is defined by a number of detector rows—1 divided by 2. In a step S210, the measured data undergoes a predetermined Hconv step, which outputs the convolved data to reconstruct two reference images. In one embodiment, the Hconv step utilizes hybrid Ramp plus Hilbert kernels. In another embodiment, the circular Feld-Kamp (CFK) technique is used to generate the two reference images. Additionally, a rebinning step is optionally added to the Hconv step to improve some image quality such as in brain shading for head imaging. In an alternative embodiment, a rebinning step and an inverse rebinning of the convolved data are optionally performed respectively prior and subsequent to the Hconv step to improve some image quality.

Subsequently, two reference images are generated. In a step S300 of one exemplary process, a first reference image CFK_A is reconstructed from the circular cone beam data using the circular Feld-Kamp (CFK) technique, and the first reference volume image CFK_A has a first field of view (FFOV). The FFOV is generally a desired back projection field of view. Similarly, in a step S220 of one exemplary process, a second reference image CFK_B is reconstructed from the circular cone beam data, and the second reference volume image CFK_B has a second field of view (SFOV), which is larger than the FFOV and optionally covers a gantry of the CT imaging system. Both of the first and second reference images CFK_A and CFK_B are now optionally stored in the respective steps S300 and S220 for later retrieval. Furthermore, the step S220 also initializes an iteration counter Iter for the subsequent instances of the steps involved in iteration.

Still referring to FIG. 7, iterative steps in the process of substantially reducing the cone beam artifact are further described in detail. In a step S230, the iteration counter Iter is incremented by one to keep track of a current instance of iteration with respect to a predetermined total number of iterations. In a step S240, a predetermined filter such as OSR filter is optionally applied to the second reference volume image CFK_B to generate an image CFK_C, which is a LLFDK-corrected CFK image. Subsequently, the image CFK_C is now volume expanded to an expanded slice CFK_D prior to differentiate the image slice in a step S255. The differentiation in the step S255 has been already described to certain extent with respect to FIGS. 3, 4 and 6 above, additional description will be provided later with respect to FIGS. 8 and 9. After differentiation in the step S255, the differentiated image is now forward projected a step S260. That is, the slice CFK_D is forward projected to output line data, and the same line data is respectively reconstructed to a line image A and a line image B in a step S310 and a step S270.

Subsequently, the line image B is optionally scaled by a line imaging scaling factor α in a step S270 for each instance of iteration. Finally, the optionally scaled line image B is combined with the second reference image CFK_B in a step S280 to generate a corrected α*LC image B in a step S290 before starting a next iteration with the optimally corrected α*LC image B in the step S230, where the iteration counter Iter is incremented.

By the same token, the line image A is also optionally scaled by the line imaging scaling factor α in the S310 for each instance of iteration. Finally, the optionaly scaled line image A is combined with the first reference image CFK_A in a step S320 to generate a corrected α* LC image A in a step S330.

With respect to the optimally corrected α*LC image A, it is determined whether or not a value of the iteration counter Iter is larger than a predetermined maximal number of iterations Niter in a step S340. If it is determined in the step S340 that the Iter counter value is not larger than the max iteration value Niter, the predetermined number of iterations has not yet been completed, and the process of substantially reducing the cone beam artifact proceeds to the step S260 for further iteration. On the other hand, if it is determined in the step S340 that the Iter counter value is larger than the max iteration value Niter, the predetermined number of iterations has been completed, and the process of substantially reducing the cone beam artifact optionally apply the LLFDK-correction in a step S350 before generating a corrected final image in a step S360. The process of substantially reducing the cone beam artifact with an adaptively optimized value of the scaling factor a is not limited to the above described steps or acts and includes other implementation steps according to the current invention.

Now referring to FIGS. 8A and 8B, exemplary images are shown to compare an original image and its differentiated image in one embodiment of differentiating an image prior to forward projection according to the current invention. FIG. 8A is an original FDK image Image [x,y,z] with a field of view of 500 mm with 512×512×320. FIG. 8B is a z difference image (DDZ) that has been generated by differentiating a difference between two slices along the z direction. According to one definition, the DDZ image is defined as follows:

$$\frac{d}{dz}\text{IMAGE}[x, y, z] = \text{IMAGE}[x, y, z+1] - \text{IMAGE}[x, y, z]$$

Figure 9A:
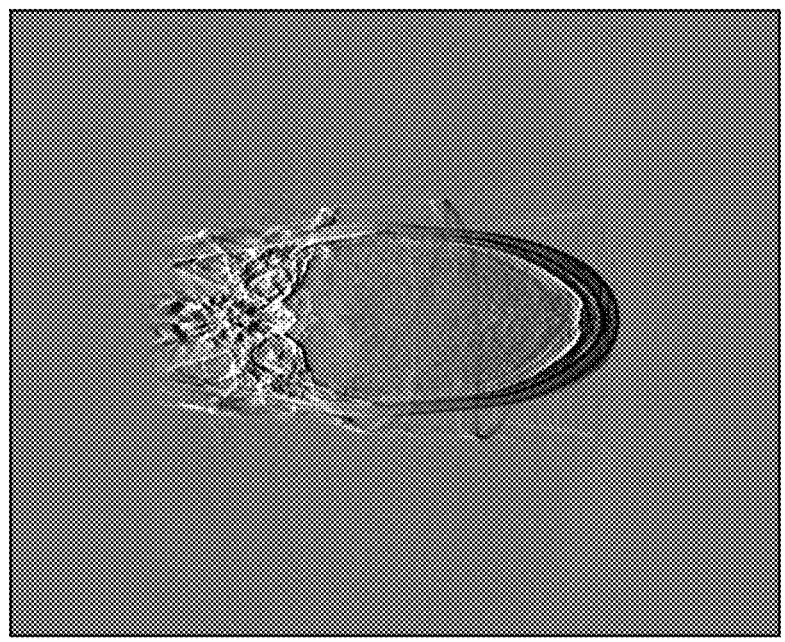

Now referring to FIGS. 9A and 9B, exemplary images are shown to compare result images in one embodiment of differentiating an image prior to forward projection according to the current invention and subsequent to forward projection. FIG. 9A is a first reconstructed image that is defined by $$\frac{d}{dh}FP[\text{IMAGE}].$$

That is, the image IMAGE was forward projected (FP) first to and then the line data is differentiated. FIG. 9B is a second reconstructed image that is defined by $$FP\left[\frac{d}{dz}\text{IMAGE}\right],$$

in which a z difference image (DDZ) is generated by differentiating a difference between two slices along the z direction and the derivative is forward projected (FP). The resulting images in FIGS. 9A and 9B are substantially the same in image quality, but the efficiency is much improved in generating the image in one exemplary process according to the current invention.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of substantially reducing cone beam artifacts, comprising:
   a) providing a first image as generated from data obtained from cone-beam circular scan;
   b) differentiating the first image to generate differentiated image;
   c) forward projecting the differentiated image to generate differentiated line data;
   d) convoluting the differentiated line data to generate the convolved data;
   e) back projecting the convolved data to generate a second image; and f) correcting the first image based upon the second image to generate a corrected image.

2. The method of substantially reducing cone beam artifacts according to claim 1 wherein the differentiated data is generated at sparse view positions.

3. The method of substantially reducing cone beam artifacts according to claim 1 wherein the differentiated data is generated for a full set of rays determined by a physical detector size.

4. The method of substantially reducing cone beam artifacts according to claim 1 wherein the differentiated data is generated for an extended set of rays determined by extended image volume based upon the first image.

5. The method of substantially reducing cone beam artifacts according to claim 1 wherein the differentiated data is generated for a limited subset of rays required for reconstructing the first image.

6. The method of substantially reducing cone beam artifacts according to claim 1 wherein the first image is differentiated along a predetermined Z direction.

7. The method of substantially reducing cone beam artifacts according to claim 1 wherein the second image is a line image.

8. The method of substantially reducing cone beam artifacts according to claim 1 wherein the first image is one of a circular Feldkamp, Davis, Kress (FDK) reconstruction image and a Hybrid convolution reconstruction (Hconv) image.

9. The method of substantially reducing cone beam artifacts according to claim 1 further comprising an additional step of iterating the steps b) through f) using the corrected image as the first image in the step b) for a predetermined number of times.

10. The method of substantially reducing cone beam artifacts according to claim 1 wherein the step a) provides a first circular image and a second circular image from the first image, the first circular image has a full field of view while the second circular image is a desired field of view.

11. A system for correcting cone beam artifacts in circular computed tomography, comprising:
a reconstruction device for reconstructing a reference image from measured data at a predetermined circular source trajectory with cone beam; and
a cone beam artifact reduction device connected to said reconstruction device for differentiating the reference image to generate differentiated reference image and generating synthetic data by forward projection of the differentiated reference image along a predetermined source trajectory, which supplements the circular source trajectory to a theoretically complete trajectory, wherein said reconstruction device reconstructs a correction image from the synthetic data and said cone beam artifact reduction device substantially reduces the cone beam artifacts by generating a corrected image using the reference image and the correction image.

12. The system for substantially reducing cone beam artifacts according to claim 11 wherein the differentiated data is generated at sparse view positions.

13. The system for substantially reducing cone beam artifacts according to claim 11 wherein the differentiated data is generated for a full set of rays determined by a physical detector size.

14. The system for substantially reducing cone beam artifacts according to claim 11 wherein the differentiated data is generated for an extended set of rays determined by extended image volume based upon the first image.

15. The system for substantially reducing cone beam artifacts according to claim 11 wherein the differentiated data is generated for a limited subset of rays required for reconstructing the first image.

16. The system for substantially reducing cone beam artifacts according to claim 11 wherein the first image is differentiated along a predetermined Z direction.

17. The system for substantially reducing cone beam artifacts according to claim 11 wherein the second image is a line image.

18. The system for substantially reducing cone beam artifacts according to claim 11 wherein the first image is one of a circular Feldkamp, Davis, Kress (FDK) reconstruction image or a Hybrid convolution reconstruction image.

19. The system for substantially reducing cone beam artifacts according to claim 11 wherein said cone beam artifact reduction device performs in a predetermined iterative manner.

* * * * *